United States Patent
Calleri (10) Patent No.: US 10,416,141 B2
(45) Date of Patent: Sep. 17, 2019

(54) METHOD AND RELATIVE SYSTEM FOR THE DETECTION AND QUANTIFICATION OF THE H2S IN DRILLING MUD

(71) Applicant: GEOLOG S.R.L., San Giuliano Milanese Milan (IT)

(72) Inventor: Antonio Calleri, Milan (IT)

(73) Assignee: GEOLOG S.R.L., San Giuliano Milanese (Milan) (IT)

( * ) Notice: Subject to any disclaimer, the term of this patent is extended or adjusted under 35 U.S.C. 154(b) by 240 days.

(21) Appl. No.: 15/386,722

(22) Filed: Dec. 21, 2016

(65) Prior Publication Data

US 2017/0176404 A1    Jun. 22, 2017

(30) Foreign Application Priority Data

Dec. 22, 2015   (IT) ................. 10201586534

(51) Int. Cl.
*G01N 33/28*     (2006.01)
*G01N 33/00*     (2006.01)
(Continued)

(52) U.S. Cl.
CPC ....... *G01N 33/0044* (2013.01); *E21B 47/065* (2013.01); *E21B 49/005* (2013.01);
(Continued)

(58) Field of Classification Search
CPC ..... E21B 47/065; E21B 49/005; G01N 27/06; G01N 33/0044; G01N 33/2823;
(Continued)

(56) References Cited

U.S. PATENT DOCUMENTS 4,124,475 A * 11/1978 Zetter .................. E21B 49/005
                                                        204/406
4,157,283 A    6/1979 Zetter
(Continued)

OTHER PUBLICATIONS

Bohnke et al. Solid State Ionics, vol. 262, Nov. 22, 2013, pp. 279-282.*

(Continued)

*Primary Examiner* — Maureen Wallenhorst
(74) *Attorney, Agent, or Firm* — Young & Thompson (57) ABSTRACT

Method for the detection and quantification of the $H_2S$ which measures concentration of the $H_2S$ in the drilling mud including the steps of measurement of the initial concentrations of $H_2S$ in free form and of the hydrogen sulphide $HS^-$ and sulphide $S^{2-}$ ion species, dissolved in the sample of mud; acidification of the sample of mud, to generate gaseous $H_2S$, making the hydrogen sulphide ($HS^-$) and sulphide ($S^{2-}$) ions dissolved in the mud and the $H_2S$ precipitated in solid form in the scavengers react; measuring concentration of the gaseous $H_2S$ formed following the first acidification; and relative system including at least: a mud sample collector; a unit measuring concentration of the hydrogen sulphide $HS^-$ and sulphide $S^{2-}$ ion species in the sample; a unit for measuring concentration of the free $H_2S$; a unit to acidify the sample of mud; electronic controller and storage and processing of the measurements made.

14 Claims, 4 Drawing Sheets

(51) Int. Cl.
*G01N 27/06* (2006.01)
*E21B 47/06* (2012.01)
*E21B 49/00* (2006.01)

(52) U.S. Cl.
CPC .......... *G01N 27/06* (2013.01); *G01N 33/287* (2013.01); *G01N 33/2823* (2013.01); *Y10T 436/184* (2015.01)

(58) Field of Classification Search
CPC . G01N 33/287; Y10T 436/18; Y10T 436/182; Y10T 436/184
USPC .......... 436/25, 30, 31, 32, 33, 119, 120, 121
See application file for complete search history.

(56) References Cited

U.S. PATENT DOCUMENTS

| | | | |
|---|---|---|---|
| 5,313,819 A | 5/1994 | Hale | |
| 6,939,717 B2 * | 9/2005 | Jiang | E21B 47/011 436/121 |
| 7,025,138 B2 * | 4/2006 | Kurkjian | E21B 49/081 166/113 |
| 8,556,001 B2 * | 10/2013 | Calleri | E21B 21/067 175/207 |
| 8,596,380 B2 * | 12/2013 | Leonard | G01N 33/287 166/250.01 |
| 10,025,000 B2 * | 7/2018 | Monteiro | E21B 49/08 |

OTHER PUBLICATIONS

David M. Hadden, "A System for Continuous On-Site Measurement of Sulfides in Water-Base Drilling Muds", Pro. SPE Sour Gas and Crude symposium, 1977, pp. 81-92, XP055295087.
Garrett et al., "Chemical Scavengers for Sulfides in Water-Base Drilling Fluids", Journal of Petroleum Technology, Jun. 1979, pp. 787-796.
Steven H. Calmer, "H2S Detector Aids Drilling Safety", Oil and Gas Journal, p. 160, Nov. 19, 1979.
Garrett: "A New Field Method for the Quantitative Determination of Sulfides in Water-Base Drilling Fluids", Journal of Petroleum Technology, vol. 29, No. 09, Sep. 1977, pp. 1195-1202, XP055295096.

* cited by examiner

METHOD AND RELATIVE SYSTEM FOR THE DETECTION AND QUANTIFICATION OF THE H2S IN DRILLING MUD

FIELD OF THE INVENTION

The present invention relates to a method and relative system for the detection and quantification of the H$_2$S in drilling mud.

BACKGROUND OF THE INVENTION

The technical area whereto the present invention belongs is that of monitoring of drilling wells for the exploitation of the hydrocarbon resources of the subsoil.

Among the activities of monitoring of the wells special importance is represented by the analysis of the gases extracted from the drilling muds. This analysis supplies information both on the nature of the state of the drilled rock and on the possible hydrocarbon resources present.

All the gases extracted from the drilling muds comprise both hydrocarbons and non-hydrocarbon species. Among the latter particular importance is assumed by hydrogen sulfide H$_2$S, due to its toxicity to humans and its aggressiveness and corrosiveness for equipment. For this reason, when the presence of H$_2$S is detected or presumed in the subsoil during drilling, additives are fed into the drilling mud, known in the art as "scavengers", which, reacting with the H$_2$S in gaseous form, form solid precipitates, in this way neutralising the toxic and aggressive action of the H$_2$S.

In addition to the reasons stated above, relating to the hazardous nature of the H$_2$S, detection of the presence of the H$_2$S is important for better characterisation of the zone of exploration from the geological viewpoint and obtaining, in this way, information useful for exploitation of the hydrocarbon resources.

At the state of the art, one of the best known systems for the detection of the H$_2$S in the drilling mud is the device known in the art as "mud duck", described in Calmer S. H. "H$_2$S Detector Aids Drilling Safety", Oil and Gas Journal, page 160, Nov. 19, 1979 and in Hadden D. M. "A system for continuous on-site measurement of sulphides in water-base drilling muds", Proc. SPE Sour Gas and Crude symposium 1977. This system comprises a probe which contains three electrochemical sensors: two for the measurement of the concentration of the ion species derived from the reaction of the H$_2$S with the drilling mud and a third sensor for measuring temperature. Since said mud is generally characterised by a basic pH, the gaseous H$_2$S present in the subsoil reacts with it, giving rise to the formation of the HS$^-$ and S$^{2-}$ ion species, which remain dissolved in the mud itself. The first of the sensors of the mud duck system therefore measures the concentration of the hydrogen ion [H$^+$], and the second the concentration of the sulphide [S$^{2-}$] ions. The concentration of the hydrogen sulphide [HS$^-$] ion is calculated from the concentration of the sulphide ions [S$^{2-}$] and of the hydrogen ion [H$^+$], by means of the following well known equation:

$$K_1 = \frac{[H^+][S^{2-}]}{[HS^-]} \approx 10^{-13} \qquad (i)$$

where [H$^+$], The concentrations of hydrogen ion [H$^+$], and of the sulphide [S$^{2-}$] ions are, in their turn, not the values directly measured by the sensors, but are estimated starting from the values directly measured by the sensors through the following well known Nernst equations:

$$E_{S^{2-}} = E_0 + \frac{RT}{nF} \log_e [S^{2-}] \qquad (ii)$$

$$E_{H^+} = E_0 + \frac{RT}{nF} \log_e [H^+] \qquad (iii)$$

where E$_0$ is the reference potential, n the charge of the ion being measured, F the Faraday's number, R the gas constant and T the temperature in ° C.

One of the disadvantages of the mud duck system arises from the fact that, in order to measure the concentration of the H$^+$, and hence of the HS$^-$, and S$^{2-}$ species, the probe of the mud duck is immersed in the drilling mud collected in the tank of the vibrating screens. For greater clarity it is recalled here that when the drilling mud rises to the surface it flows along a pipe known as "flow line" which ends in a tank where a system of vibrating screens separates the fluid component of the mud from the drilling debris, said fluid component being then destined to be returned into circulation in the drilled hole. This tank constitutes an environment strongly unfavourable to measurements performed by the probe of the mud duck system. It is in fact not unusual for this probe to be contaminated to the extent of becoming unusable, unless adequately cleaned. For a correct use of the mud duck it is therefore necessary to provide for regular maintenance for the cleaning of the probe.

A second system, known in the art as "Garrett Gas Train", and described in Garrett L., Clark R. K., Carney L. L. and Grantham C. K. "Chemical Scavengers for Sulfides in Water Based Drilling Fluids", Journal of Petroleum Technology, June, 1979, page 787, provides for the filtrate of the drilling mud to be subjected to acidification, so that the hydrogen sulphide (HS$^-$) and sulphide (S$^{2-}$) ions react, giving rise to free H$_2$S. The latter is transported by a carrier gas into a special chamber where, by means of colorimeter vials, an indication is obtained of the quantity of H$_2$S present in the mud. It is clear that such a type of measurement, while having the advantage, with respect to the previous one relating to the mud duck system, of having been performed in an isolated environment, does not have high precision, due to the inevitable intrinsic limits of the colorimeter vials. The principle of functioning of the latter is based, in fact, on the change in colour of an appropriate reagent, following the reaction with the H$_2$S. The length of the coloured part of the vial is proportional to the concentration of the H$_2$S. The estimate of the latter is therefore made by comparing visually the length of the coloured part with a concentration scale printed on the vial. A quantification of this type is evidently subject to the errors which always accompany every measurement which is based on valuations performed by a human operator.

SUMMARY OF THE INVENTION

The object of the present invention is therefore that of providing a method and relative system for the detection and the quantification of the H$_2$S in the drilling mud which allows operation in a controlled environment and therefore free from contaminations and which, at the same time, is able to provide a reliable estimate of the concentration of H$_2$S in the drilling mud.

Among the further disadvantages of the systems of the prior art, in particular of those based on the use of colorimeter vials, there is the impossibility of performing checks on the possible success of the acidification in freeing all the $H_2S$, whether dissolved in ionic form in the fluid part of the mud or precipitated in solid form in the scavengers. In fact, with an acidification, performed in a single step and without any check on the reaching of equilibrium, and performing spot measurements of the ion species, it is not possible to have the certainty of having freed, and effectively measured, all the $H_2S$ effectively present in the mud. Consequently the quantity of $H_2S$ estimated could be smaller than the quantity of $H_2S$ really present.

A second object of the present invention is therefore that of providing a method and relative system for the detection and the quantification of the $H_2S$ in the drilling mud which allows the repetition several times and in a continuous manner of the measurements of the $H_2S$ present in a certain sample of mud and to check that all the $H_2S$ present in the mud, whether dissolved in ionic form or precipitated in solid form, is freed following acidification of the mud itself. Thanks to this check, the method and the relative system of the present invention avoid the risk of the quantity of $H_2S$ being underestimated.

A further disadvantage of the systems of the prior art, in particular of those based on the use of electrochemical sensors, consists of the errors of estimate of the concentration of $H^+$, and hence of the $HS^-$, and $S^{2-}$ ions, due to the lack of consideration of the possible variations of ionic force which may take place inside the electrolytic cell which constitutes the sensor. It is known in fact that the variations of the potential of an electrolytic cell can be considered as due exclusively to the variations of concentration of the ion species which are being measured, only if the ionic force is constant. Therefore a possible variation of the latter, if not considered appropriately, entails the occurrence of errors in the measurements of concentration.

A third object of the present invention is therefore that of providing a method and relative system for the detection and the quantification of the $H_2S$ in the drilling mud which provides a check of the variations of the ionic force, as well as a compensation of the measurements of concentration of $H^+$, and then of the $HS^-$, and $S^{2-}$ species for possible variations of said force.

These and further objects are achieved by the present invention by means of a method which provides for the measurement of the concentration of the $H_2S$ in the drilling mud by means of an analysis of a sample of said mud comprising at least the following steps:

measurement of the initial concentrations of $H_2S$ in free form and of the hydrogen $H^+$, hydrogen sulphide $HS^-$ and sulphide $S^{2-}$ ion species, dissolved in said sample of mud;

mechanical stirring of said sample of mud;

measurement of the concentration of gaseous $H_2S$ freed following said stirring;

first acidification of the sample of mud, the object of said first acidification being that of making the hydrogen sulphide ($HS^-$) and sulphide ($S^{2-}$) ions dissolved in the mud and the $H_2S$ precipitated in solid form in the scavengers react, thus generating gaseous $H_2S$;

measurement of the concentration of said gaseous $H_2S$ formed following said first acidification;

optionally, second acidification of the sample of mud, the object of said second acidification being to make a possible residual quantity of $HS^-$ and $S^{2-}$ ions dissolved in the mud and a possible residual quantity of $H_2S$ precipitated in solid form react, further freeing gaseous $H_2S$;

measurement of the concentration of said free $H_2S$ formed following said second acidification.

Hereinafter, the expression "measurement of the hydrogen sulphide $HS^-$ and sulphide $S^{2-}$ ion species" should not be intended in the strict sense of "direct measurement" but in its wider sense. Indeed, it is well known in the field, that the concentrations of the above mentioned ion species cannot be measured directly, but by applying the equation (iii) in the case of the sulphide $S^{2-}$ ions and, the equation (ii), (iii) and then (i), in the case of the hydrogen sulphide $HS^-$ ions.

The method described above can be implemented by a system which comprises at least:
  means for the collection of a sample of mud;
  means for the measurement of the concentration of the hydrogen sulphide $HS^-$ and sulphide $S^{2-}$ ion species in said sample of mud;
  means for measuring the concentration of the free $H_2S$;
  means for the acidification of said sample of mud;
  electronic means for control of the entire system;
  means for the storage and processing of the measurements made Hereinafter, the word "measurement" in the expression "means of measurement of the hydrogen sulphide $HS^-$ and sulphide $S^{2-}$ ion species" should not be intended, in the strict sense of "direct measurement", but in its wider sense. Indeed, it is well known in the field that the hydrogen sulphide $HS^-$ cannot be measured directly, but by measuring the cell potential of electrochemical sensors and by subsequently applying the equation (iii) in the case of the sulphide $S^{2-}$ ions and the equation (ii), (iii) and then (i) in the case of the hydrogen sulphide $HS^-$ ions.

These and other aspects will be made clearer by the following description, relating to some preferred embodiments of the present invention to be considered by way of a non-limiting example of the more general concept claimed.

BRIEF DESCRIPTION OF THE DRAWINGS

The following description refers to the accompanying drawings, in which.

DETAILED DESCRIPTION OF THE PREFERRED EMBODIMENTS

Figure 1:
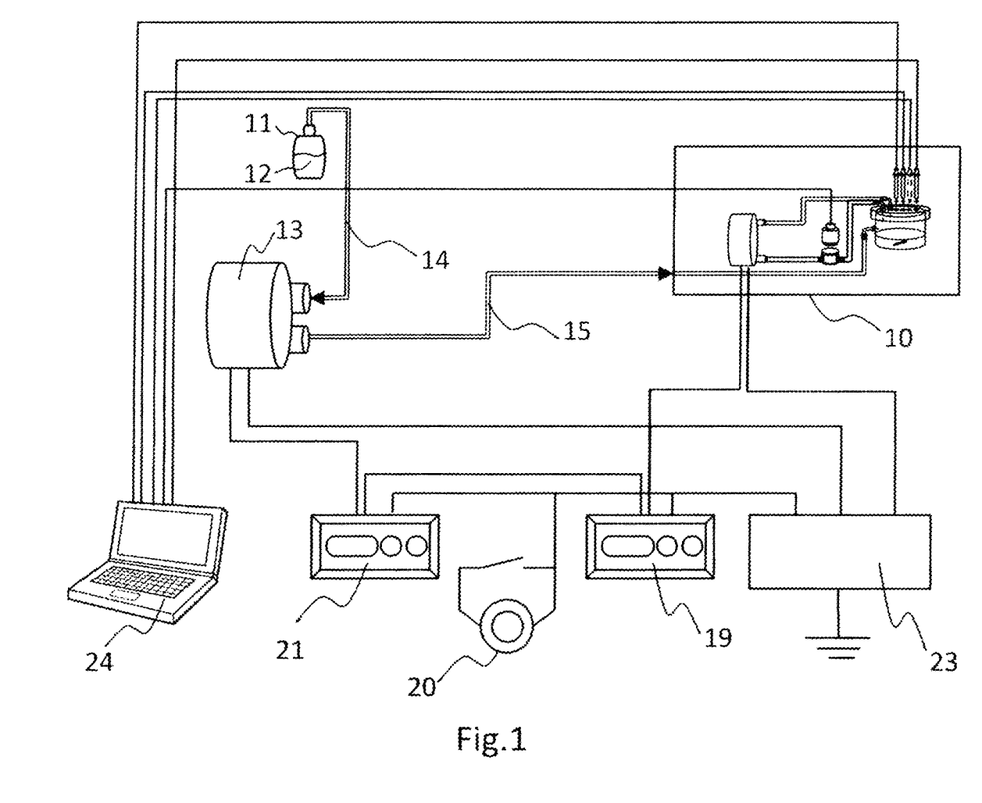
FIG. 1 is a diagram showing the system which implements the method which is the object of the present invention.
Figure 2:
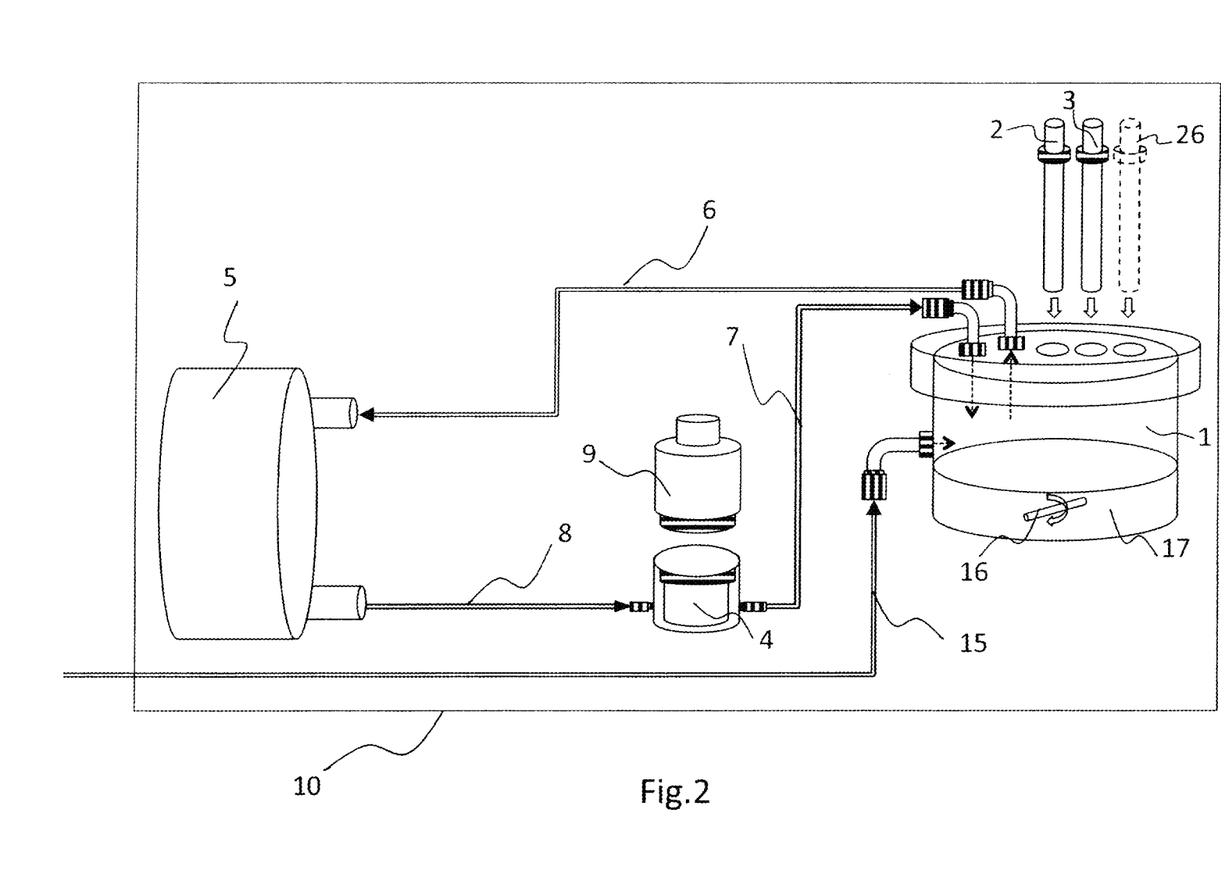
FIG. 2 is a simplified representation of a detail of a first embodiment of the system of the present invention, relating to the sampling cell of the system, wherein said sampling cell is thermostat controlled.
Figure 3:
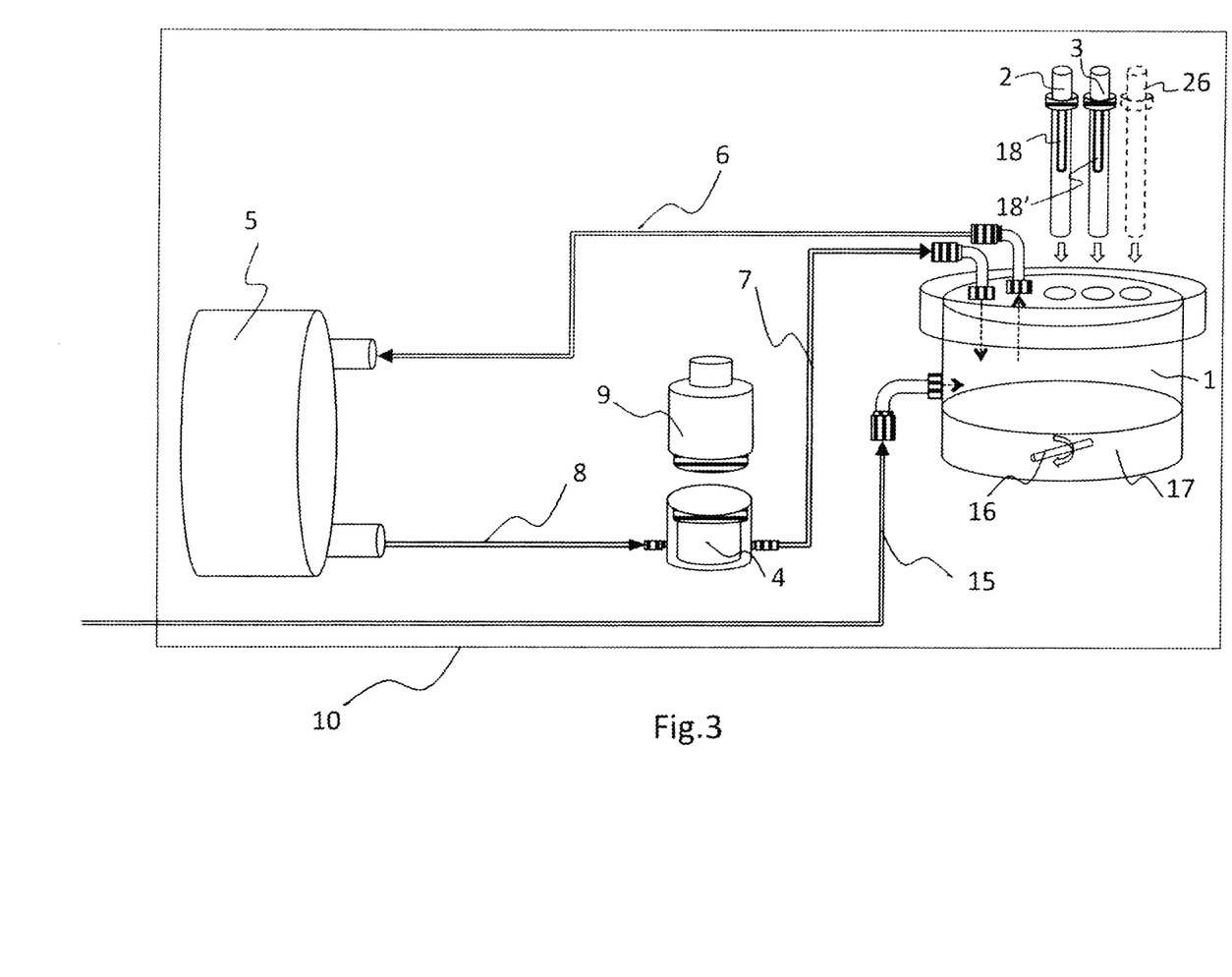
FIG. 3 is a simplified representation of a detail of a second embodiment of the system of the present invention, relating to the sampling cell of the system, wherein said means for the measurement of the concentration of the hydrogen sulphide $HS^-$ and sulphide $S^{2-}$ ion species (2, 3) in said mud sample (17) comprise means for the measurement of the temperature (18, 18', 28) in said sample of mud (17), said means (18, 18', 28) being integrated with said means for the measurement of the concentrations of the $HS^-$ and $S^{2-}$ ion species (2, 3)
Figure 4:
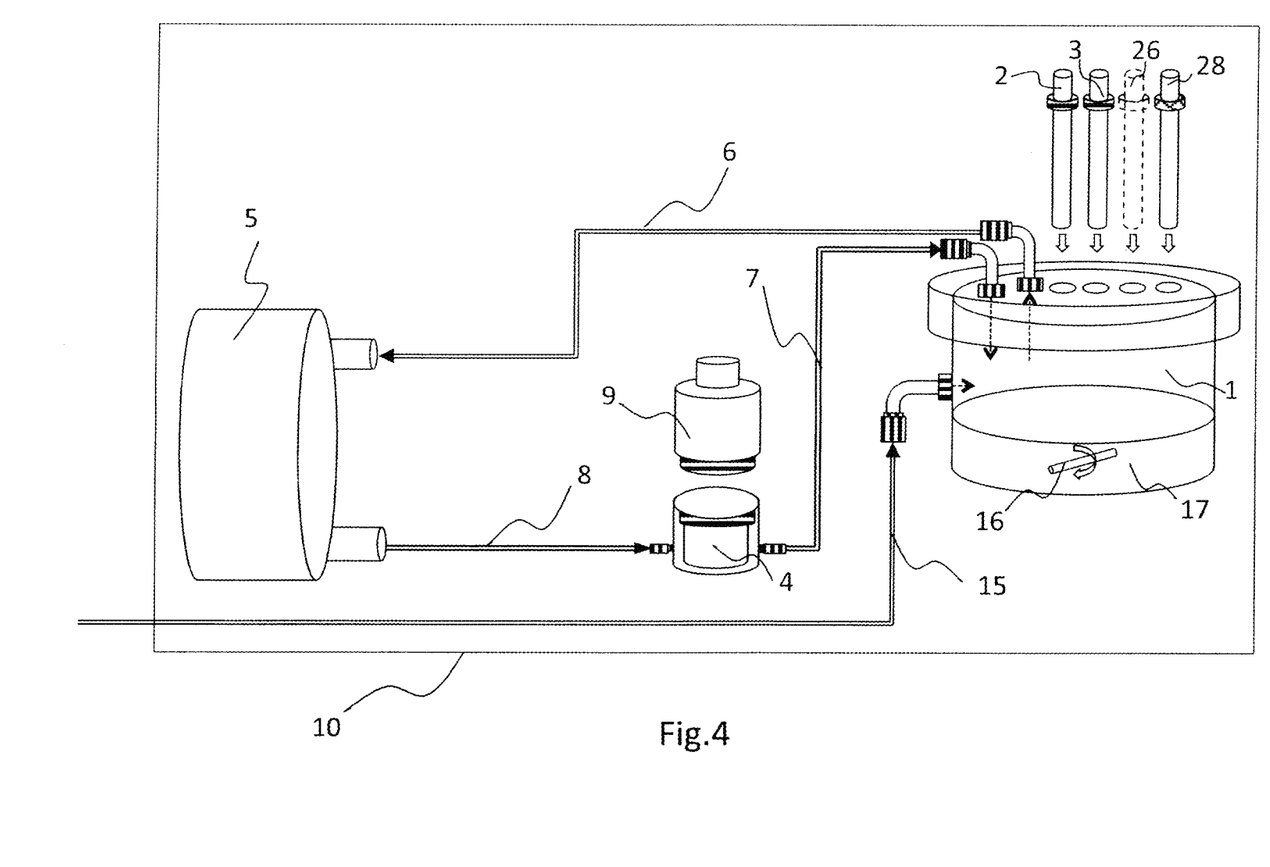
FIG. 4 is a simplified representation of a detail of a third embodiment of the system of the present invention, relating to the sampling cell of the system.

Referring to FIGS. 2, 3 and 4, a first embodiment of the method of the present invention provides for the following steps:

taking of a sample of drilling mud (17);
placing of said sample of mud (17) in a sampling chamber (1);
measurement of the concentration of gaseous $H_2S$ in free form present in the head space of the sampling chamber;
measurement of the concentration of the hydrogen sulphide $HS^-$ and sulphide $S^{2-}$ ion species, dissolved in said sample of mud;
first mechanical stirring of said sample of mud;
measurement of the concentration of gaseous $H_2S$ in free form, said $H_2S$ being freed following said first stirring;
first acidification of the sample of mud, said first acidification being apt to make the hydrogen sulphide ($HS^-$) and sulphide ($S^{2-}$) ions dissolved in the mud and the $H_2S$ precipitated in solid form in the scavengers react, thus generating gaseous $H_2S$;
second mechanical stirring of said sample of mud;
repetition of a cycle of steps comprising:
 taking of a gaseous sample;
 measurement of the concentration of free $H_2S$ in said gaseous sample, said free $H_2S$ being generated following said first acidification; and
 returning of said gaseous sample in the sampling chamber (1); said repetition being performed until the measurement of the concentration of the free $H_2S$ in said gaseous sample does not vary with respect to the measurement of the concentration of the free $H_2S$ in said gaseous sample, performed in the previous cycle;
  conversion of the measurement of the volumetric concentration of the $H_2S$ in the gaseous sample into a measurement of volumetric concentration of the $H_2S$ in the mud.

Referring to FIGS. 2, 3 and 4, a second embodiment of the method of the present invention provides for the following steps:
taking of a sample of drilling mud (17);
placing of said sample of mud (17) in a sampling chamber (1);
measurement of the concentration of gaseous $H_2S$ in free form present in the head space of the sampling chamber;
measurement of the concentration of the hydrogen sulphide $HS^-$ and sulphide $S^{2-}$ ion species, dissolved in said sample of mud;
first mechanical stirring of said sample of mud;
measurement of the concentration of the gaseous $H_2S$ in free form, said $H_2S$ freed following said first stirring;
first acidification of the sample of mud, said first acidification being apt to make the hydrogen sulphide ($HS^-$) and sulphide ($S^{2-}$) ions dissolved in the mud and the $H_2S$ precipitated in solid form in the scavengers react, thus generating gaseous $H_2S$;
second mechanical stirring of said sample of mud;
repetition of a cycle of steps comprising:
 taking of a gaseous sample;
 measurement of the concentration of free $H_2S$ in said gaseous sample, said free $H_2S$ being generated following said first acidification; and
 returning of said gaseous sample in the sampling chamber (1); said repetition being performed until the measurement of the concentration of the free $H_2S$ in said gaseous sample does not vary with respect to the measurement of the concentration of the free $H_2S$ in said gaseous sample, performed in the previous cycle;
second acidification of the sample, said second acidification being apt to make a possible residual quantity of $HS^-$ and $S^{2-}$) ions dissolved in the mud and a possible residual quantity of $H_2S$ precipitated in solid form react, thus freeing, further, gaseous $H_2S$;
third mechanical stirring of said sample of mud;
repetition of a cycle of steps comprising:
 taking of a gaseous sample;
 measurement of the concentration of free $H_2S$ in said gaseous sample, said free $H_2S$ being generated following said first acidification; and
 returning of said gaseous sample in the sampling chamber (1); said repetition being performed until the measurement of the concentration of the free $H_2S$ in said gaseous sample does not vary with respect to the measurement of the concentration of the free $H_2S$ in said gaseous sample, performed in the previous cycle;
  conversion of the measurement of the volumetric concentration of the $H_2S$ in the gaseous sample into a measurement of volumetric concentration of the $H_2S$ in the mud.

Referring to FIGS. 2, 3 and 4, a third embodiment of the method of the present invention provides for the following steps:
taking of a sample of drilling mud (17);
placing of said sample of mud (17) in a sampling chamber (1);
measurement of the concentration of gaseous $H_2S$ in free form present in the head space of the sampling chamber;
measurement of the concentration of the hydrogen sulphide $HS^-$ and sulphide $S^{2-}$ ion species, dissolved in said sample of mud;
first mechanical stirring of said sample of mud;
measurement of the concentration of the gaseous $H_2S$ in free form, said $H_2S$ being freed following said first stirring;
first acidification of the sample of mud, said first acidification being apt to make the hydrogen sulphide ($HS^-$) and sulphide ($S^{2-}$) ions dissolved in the mud and the $H_2S$ precipitated in solid form in the scavengers react, thus generating gaseous $H_2S$;
second mechanical stirring of said sample of mud;
taking of a gaseous sample;
measurement of the concentration of free $H_2S$ in said gaseous sample, said free $H_2S$ being generated following said first acidification;
second acidification of the sample, said second acidification being apt to make a possible residual quantity of $HS^-$ and $S^{2-}$) ions dissolved in the mud and a possible residual quantity of $H_2S$ precipitated in solid form react, further freeing gaseous $H_2S$;
third mechanical stirring of said sample of mud;
repetition of a cycle of steps comprising:
 taking of a gaseous sample;
 measurement of the concentration of free $H_2S$ in said gaseous sample, said free $H_2S$ being generated following said second acidification; and
 returning of said gaseous sample in the sampling chamber (1); said repetition being performed until the measurement of the concentration of the free $H_2S$ in said gaseous sample does not vary with respect to the measurement of the concentration of the free $H_2S$ in said gaseous sample, performed in the previous cycle;

conversion of the measurement of the volumetric concentration of the $H_2S$ in the gaseous sample into a measurement of volumetric concentration of the $H_2S$ in the mud.

Should for the measurement of the concentration of the hydrogen sulphide $HS^-$ and sulphide $S^{2-}$ ion species use not be made either of a thermostat-controlled container for the collection of the mud sample or means for the measurement of the concentration of the ions able to perform automatic compensation for possible temperature variations, the method of the present invention will also provide a step of postprocessing subsequently the measurements of concentration of the $HS^-$ and $S^{2-}$ ion species, said step of postprocessing consisting of the compensation of the measurements of concentration on the basis of the measurement of the temperature.

The method of the present invention can further provide a step of measurement of the electrical conductivity of the solution made up of the sample of mud. Said step of measurement of the electrical conductivity is aimed at the control of the measurements of concentration of the $HS^-$ and $S^{2-}$ ion species. As will be further explained here below, with reference to the system which implements the method of the present invention, the concentrations of the $HS^-$ and $S^{2-}$ species are measured by measuring the variations of the potential of two electrochimicalcells from the prior art. The first one for the hydrogen ions $H^+$ and the second one for the sulphide ions $S^{2-}$ Since it is known that the variations in the cell potential, supposing the temperature to be constant, can be said to be due exclusively to the variations in concentration of the ion species only if the ionic force is also constant, it is necessary to check that this condition is respected or that a compensation is performed for possible variations in said force. Since the ionic force can be estimated by measuring the electrical conductivity of a solution, monitoring said conductivity, the measurements of concentration can be compensated and thus a correct estimate obtained of the real concentration of $HS^-$ and $S^{2-}$ ions.

Referring to FIGS. 1, 2, 3 and 4, the system of the present invention, which allows implementation of the method described above, comprises:
  means for the collection (1) of a sample of mud (17);
  means for the measurement of the concentration of the hydrogen sulphide $HS^-$ and sulphide $S^{2-}$ ion species (2, 3), in said sample of mud (17);
  means for measuring the concentration of the free $H_2S$ (4, 5, 6, 7, 8, 9);
  means for the acidification (11, 12, 13, 14, 15) of said sample of mud (17);
  electronic means of control (19, 20) of said means for the measuring of the concentration of the free $H_2S$ (4, 5, 6, 7, 8, 9);
  electronic means of control (21, 22) of said means for the acidification (11, 12, 13, 14, 15) of said sample of mud (17);
  means of electrical supply (23) of said means for the acidification (11, 12, 13, 14, 15) and of said means for the measuring of the concentration of the free $H_2S$ (4, 5, 6, 7, 8, 9), as well as of said electronic means of control (19, 20, 21, 22) of said means for the measuring of the concentration of the free $H_2S$ (4, 5, 6, 7, 8, 9) and of said means for the acidification (11, 12, 13, 14, 15);
  means for the storage and processing (23, 24) of the measurements made by said means for the measurement of the concentration of the hydrogen sulphide $HS^-$ and sulphide $S^{2-}$ ion species (2, 3) in said sample of mud (17);

Said means for the collection (1) of a sample of mud comprise a sampling chamber (1);
Said means for measuring the concentration of the free $H_2S$ (4, 5, 6, 7, 8, 9) comprise:
  a flow chamber (4);
  a first pump (5) apt to the taking of a gaseous sample from said sampling chamber (1) and apt to the sending of said gaseous sample to said flow chamber (4);
  pipes (6) for the transfer of the gaseous sample from said sampling chamber (1) to said first pump (5);
  pipes (7) for the transfer of said gaseous sample from said first pump (5) to said flow chamber (4);
  pipes (8) for the transfer of said gaseous sample from said flow chamber (4) to said sampling chamber (1); and
  an electrochemical sensor (9) for measuring the concentration of the $H_2S$ in said gaseous sample contained in said flow chamber (4), said gaseous sample having been taken from said sampling chamber (1) and sent to said flow chamber (4) by means of said first pump (5).

Said first pump (5), said flow chamber (4) and said sampling chamber (1) form a so-called sampling cell (10).
Said means for the acidification (11, 12, 13, 14, 15) of said sample of mud (17) comprise:
  a strong acid (11), preferably hydrochloric acid HCl;
  a container (12) for the collection of said strong acid;
  a second pump (13) apt to the taking of said strong acid (11) from said container (12) for the collection of said strong acid (11) and apt to the sending of said strong acid (11) to said sampling chamber (1);
  pipes (14) for the transfer of said strong acid (11) from said container (12) for the collection of said strong acid (11) to said second pump (13); and
  pipes (15) for the transfer of said strong acid (11) from said second pump (13) to said sampling chamber (1).

The system of the present invention can moreover comprise also: mechanical means (16) for the facilitation of the freeing of gaseous $H_2S$ from said sample of mud. Said mechanical means (16) for the facilitation of the freeing of gaseous $H_2S$ from said sample of mud (17) comprise, in turn, a magnetic stirring bar (16) placed inside said sampling chamber (1).

In a first embodiment of the system of the present invention, which does not necessarily implement the first embodiment of the method of the present invention but can be used to implement the first, the second and the third embodiments of the method of the present invention, said sampling chamber (1) is a thermostat-controlled cell, i.e. able to maintain in its interior a constant temperature.

Referring to FIG. 2, in a second embodiment of the system of the present invention, which does not necessarily implement the second embodiment of the method of the present invention, but can be used to implement the first, the second and the third embodiments of the method of the present invention, said means for the measurement of the concentration of the hydrogen sulphide $HS^-$ and sulphide $S^{2-}$ ion species (2, 3) in said sample of mud (17) comprise means for the measurement of the temperature (18, 18', 28) in said sample of mud (17), said means (18, 18', 28) being integrated with said means for the measurement of the concentrations of the $HS^-$ and $S^{2-}$ ion species (2, 3). More particularly said means for the measurement of the concentrations of the $HS^-$ and $S^{2-}$ ion species (2, 3) are provided with an electrochemical sensor and with a sensor (18, 18') for the measurement of the temperature, known in the art as "internal temperature compensation sensor".

Referring to FIG. 3, in a third embodiment of the system of the present invention, which does not necessarily implement the third embodiment of the method of the present invention, but can be used to implement the first, the second and the third embodiments of the method of the present invention, said system comprises means for the measurement of the temperature (18, 18', 28) in said sample of mud (17), said means (18, 18', 28) being separate from said means for the measurement of the concentrations of the $HS^-$ and $S^{2-}$ ion species In this case the system will also comprise a probe (28) for the measuring of the temperature, separate from the means (2, 3) for the measurement of the ion species, and means for the storage and processing (25) of the measurements taken by said probe (28) for the measuring of the temperature, said means for the postprocessing (25) being apt to perform subsequently the compensation of the measurement of the concentration of $HS^-$ and $S^{2-}$ species for the temperature variations.

Referring to FIGS. 2, 3 and 4, the system of the present invention may also comprise, in all three of its embodiments, means for the measurement of the electrical conductivity (26) in the sample of mud (17).

In this case the system will also comprise means for the storage and processing (27) of the measurements made by said means for the measurement of electrical conductivity (26), said means for the processing (27) being apt to perform the compensation of the measurement of the concentration of the $HS^-$ and $S^{2-}$ species for the electrical conductivity. In FIGS. 2, 3 and 4 said means for the measurement of electrical conductivity (26) are represented with a dotted line, to show that these are optional means.

The invention described above achieves the objects set, overcoming the disadvantages of the prior art.

The present invention provides in fact a system which allows the obtaining of measurements relating to the $H_2S$ in a controlled environment and at the same time, thanks to the presence of the sampling cell, offers the possibility of repeating several times, and continuously, the measurements of the $H_2S$ in a same sample of mud. This factor, together with the presence of a double acidification, means that a control can be carried out on the effective freeing in gaseous form of all the $H_2S$ present in the mud, whether dissolved in ionic form in the fluid part of the mud or precipitated in solid form in the scavengers. Finally, thanks to the measurement of the electrical conductivity in the sample of mud, it is possible to perform the compensation of the measurements of concentration for the variation in ionic force and thus obtain reliable estimates of the concentrations of the ion species derived from the dissociation of the $H_2S$ in the drilling mud.

What is claimed is:

1. A method for detection and quantification of hydrosulphuric acid $H_2S$ in a drilling mud, comprising the following steps:
   taking a sample of drilling mud
   placing said sample of mud in a sampling chamber;
   measurement of a concentration of gaseous $H_2S$ in free form present in a head space of the sampling chamber;
   measurement of a concentration of hydrogen sulphide $HS^-$ and sulphide $S^{2-}$ ion species, dissolved in said sample of mud; and
   acidification of said sample of mud,
   wherein after said step of acidification, the following steps are carried out:
   repetition of a cycle of steps that include
   taking of a gaseous sample from the head space of the sampling chamber,
   measuring a concentration of free $H_2S$ in said gaseous sample, said free $H_2S$ being generated following said acidification, and
   returning said gaseous sample to said sampling chamber,
   said repetition being performed until the measurement of the concentration of the free $H_2S$ in said gaseous sample does not vary with respect to the measurement of the concentration of the free $H_2S$ in said gaseous sample, performed in a previous cycle; and
   conversion of the measurement of the concentration of the free $H_2S$ in said gaseous sample into a measurement of concentration of the $H_2S$ in the mud.

2. The method according to claim 1, wherein said method further comprises, after said measurement of the concentration of gaseous $H_2S$ in free form present in the head space of the sampling chamber and before said step of acidification, the following steps:
   mechanical stirring of said sample of mud; and
   measurement of the concentration of free $H_2S$, in the head space of sampling chamber, wherein said measured $H_2S$ is $H_2S$ freed following said stirring.

3. The method according to claim 2, wherein said method further comprises, after said repetition of a cycle of steps, a second acidification of the sample of mud, and after said second acidification, a second repetition of said cycle of steps.

4. The method according to claim 3, wherein said method further comprises a step of measurement of temperature in said sample of mud in the sampling chamber.

5. The method according to claim 2, wherein said method further comprises, before said repetition of a cycle of steps, a second acidification of the sample of mud.

6. The method according to claim 2, wherein said method further comprises a step of measurement of temperature in said sample of mud in the sampling chamber.

7. The method according to claim 2, wherein said method further comprises, after said step of acidification and before said repetition of a cycle of steps, a second mechanical stirring of said sample of mud.

8. The method according to claim 7, wherein said method further comprises a step of measurement of temperature in said sample of mud in the sampling chamber.

9. The method according to claim 7, wherein said method further comprises, before said repetition of a cycle of steps, a second acidification of the sample of mud.

10. The method according to claim 9, wherein said method further comprises, after said second acidification, a third mechanical stirring of said sample of mud.

11. The method according to claim 9, wherein said method further comprises a step of measurement of temperature in said sample of mud in the sampling chamber.

12. The method according to claim 1, wherein said method further comprises a step of measurement of temperature in said sample of mud in the sampling chamber.

13. The method according to claim 1, wherein said method further comprises a step of measurement of electrical conductivity in said sample of mud in the sampling chamber.

14. The method according to claim 1, wherein said method further comprises, before said repetition of a cycle of steps, a second acidification of the sample of mud.

* * * * *